(12) United States Patent
Wyss

(10) Patent No.: US 6,926,738 B2
(45) Date of Patent: Aug. 9, 2005

(54) MODULAR KNEE JOINT PROSTHESIS

(75) Inventor: Joseph Wyss, Fort Wayne, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 10/779,898

(22) Filed: Feb. 17, 2004

(65) Prior Publication Data

US 2004/0162620 A1 Aug. 19, 2004

Related U.S. Application Data

(63) Continuation of application No. 10/185,492, filed on Jun. 28, 2002, now abandoned.

(51) Int. Cl.[7] ................................................. A61F 2/38
(52) U.S. Cl. .................................. 623/20.27; 623/18.11
(58) Field of Search ........................... 623/20.11, 20.13, 623/20.14, 20.15, 20.17, 20.21, 20.27, 20.28, 20.29, 20.31, 20.33, 18.11, 19.11, 23.39

(56) References Cited

U.S. PATENT DOCUMENTS

| 5,282,868 | A | | 2/1994 | Bahler |
| 5,314,483 | A | | 5/1994 | Wehrli et al. |
| 5,370,699 | A | | 12/1994 | Hood et al. |
| 5,370,701 | A | | 12/1994 | Finn |
| 5,395,401 | A | | 3/1995 | Bahler |
| 5,776,201 | A | * | 7/1998 | Colleran et al. ......... 623/20.15 |
| 5,824,103 | A | | 10/1998 | Williams |
| 5,906,643 | A | | 5/1999 | Walker |
| 6,080,195 | A | | 6/2000 | Colleran et al. |
| 6,102,954 | A | | 8/2000 | Albrektsson et al. |
| 6,117,175 | A | | 9/2000 | Bosredon |
| 6,210,445 | B1 | | 4/2001 | Zawadzki |
| 6,319,283 | B1 | | 11/2001 | Insall et al. |
| 6,458,160 | B2 | | 10/2002 | Biegun et al. |
| 6,629,999 | B1 | * | 10/2003 | Serafin, Jr. ............... 623/20.15 |
| 2001/0034554 | A1 | | 10/2001 | Pappas |

FOREIGN PATENT DOCUMENTS

| EP | 0577529 A | 1/1994 |
| FR | 2751204 | 1/1998 |

* cited by examiner

Primary Examiner—Corrine McDermott
Assistant Examiner—Thomas J Sweet
(74) Attorney, Agent, or Firm—Maginot, Moore & Beck

(57) ABSTRACT

A knee joint prosthesis includes a femoral component for engaging the femur having an articular surface and a recess within the articular surface, and a tibial component for engaging the tibia with a bore, and a meniscal component comprising a rotation pin configured for rotatable mounting within the bore of the tibial component. The meniscal component also includes a bearing surface for sliding contact with the articular surface of the femoral component and an elongated channel defined amid the bearing surface. A stabilizing post is provided that includes a base slidably mounted with the elongated channel and a spine post projecting from the base through the channel and into the recess when the articular surface is in contact with said bearing surface. The stabilizing post thus slides within the channel when contacted by the interior of the recess in the femoral component.

28 Claims, 3 Drawing Sheets

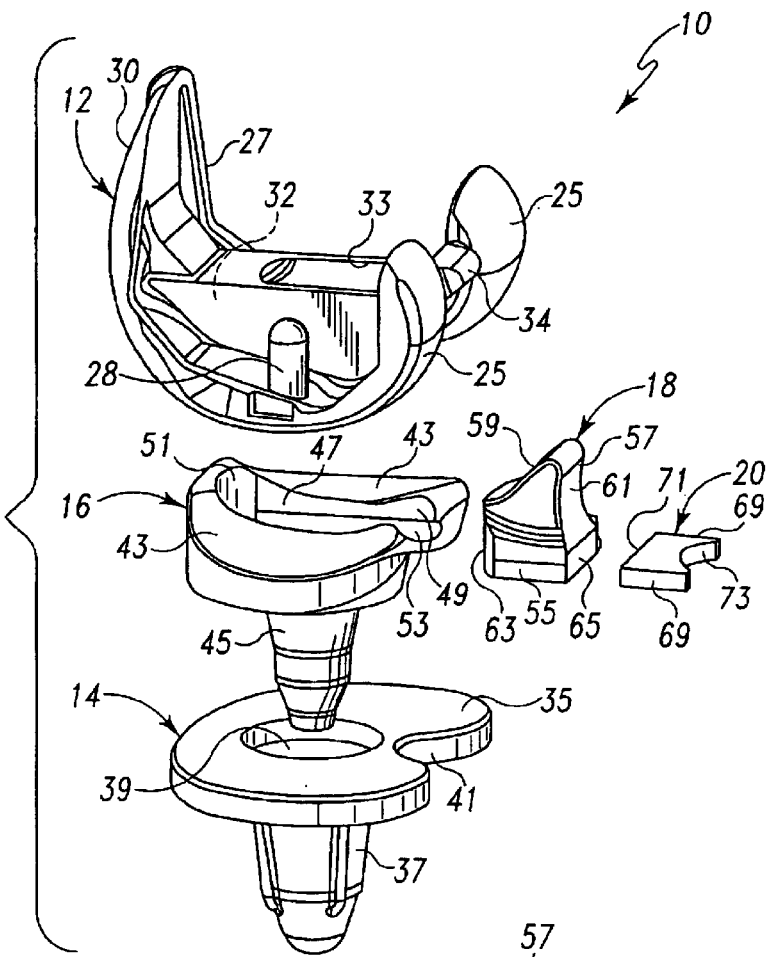
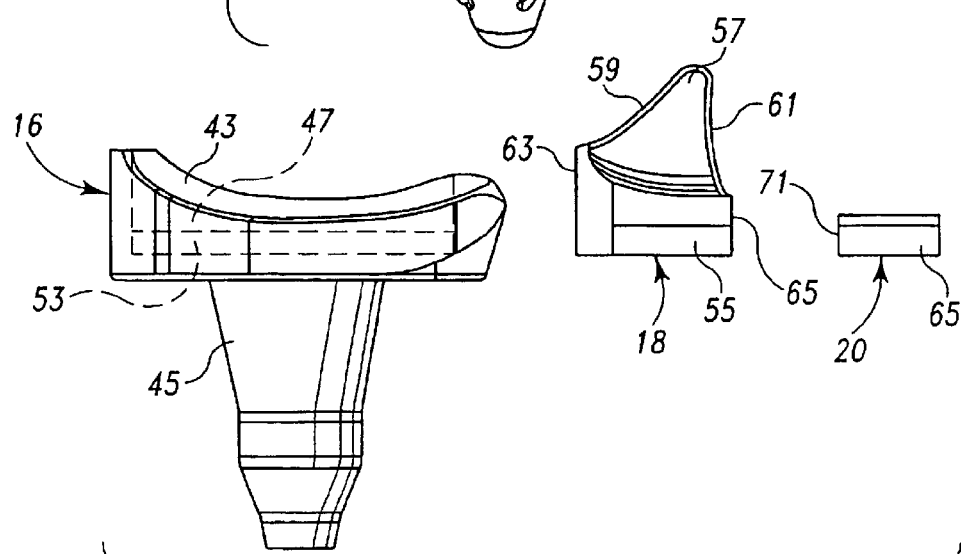
Fig. 1
Fig. 2

MODULAR KNEE JOINT PROSTHESIS

This application is a continuation of application Ser. No. 10/185,492, filed on Jun. 28, 2002, now abandoned, the disclosure of which is hereby totally incorporated by reference in its entirety.

BACKGROUND OF THE INVENTION

The present invention relates to prosthetic joints, and particularly to a prosthesis for the knee joint.

Implantable knee prostheses for diseased and/or damaged knees typically include three components, namely a femoral component, a tibial component and a meniscal component. The femoral component may also include a patellar element, or a separate patellar component may be provided. The prosthesis components are generally configured to restore or emulate as much of the natural motion of the knee joint as possible. The selection of the particular prosthesis components is usually dictated by the condition of the patient's knee. For instance, the condition of the distal end of the femur and proximal end of the tibia, as well as the patency of the surrounding ligaments and soft tissue can affect the form of the joint prosthesis.

Generally, a total knee joint replacement includes a tibial component having a platform portion which replaces the entire superior surface of the tibial plateau and substitutes for the tibial condylar surfaces. The femoral component also includes laterally-spaced condylar portions joined by an intercondylar bridge and a patellar surface.

The tibial component typically includes a tibial tray and stem for surgical attachment to the proximal end of the tibia. The component also includes an intermediate articulating surface member that is connected to the tibial tray. The intermediate member defines a bearing surface for articulation of the femoral component thereon. The mating surfaces are smoothly curved in the anterior-posterior (AP) direction to generally match the lateral profile of the natural femoral and tibial condyles, and to ultimately replicate the normal joint movement.

This normal joint movement includes a translational component in the AP direction, as well as a rolling of the femoral condyles on the tibial condyles when the knee is flexed. In addition, the natural tibia is capable of rotation relative to the femur about the axis of the tibia. Thus, an ideal knee prosthesis will be able to achieve all three degrees of freedom of movement. In some cases, the patient's knee lacks adequate posterior support due to a deficient posterior cruciate ligament. In these cases, the modular knee is preferably posteriorly stabilized, meaning that posterior movement of the tibia relative to the femur is restricted. This posterior stabilization can be achieved in a typical implant by a projection or eminence on the tibial insert that engages a box-like intercondylar portion of the femoral component. Intact collateral ligaments keep the projection within the box-like portion as the knee is flexed to inhibit dislocation of the joint at hyper-extension or hyper-flexion.

In order to increase the lifetime of the prosthetic knee joint, the mating bearing surfaces between the tibial and femoral components generally permit a combination of rolling and translational movement as the knee joint is flexed. These two degrees of freedom of movement change the direction of forces transmitted through the two components so the force transmitted through the joint is not focused on one location. In response to this optimum design aspect, some prosthetic knees include a translating intermediate bearing component. One problem with modular implants of this type is that the articulating and sliding components can be exposed to the soft tissue surrounding the joint.

SUMMARY OF THE INVENTION

In one embodiment of the invention, a modular joint prosthesis comprises a first joint component having a bone engaging portion, an articular surface, and a recess defined within the articular surface. The prosthesis further includes a mating component having a bone engaging portion and defining a bearing surface for sliding contact with the articular surface of the first joint component. In one feature of the invention, a stabilizing post is slidably mounted to the mating component amid the bearing surface with the post projecting from the mating component and into the recess when the articular surface is in contact with the bearing surface.

In certain embodiments, the mating component includes a second joint component including the bone engaging portion and an intermediate component connected to the second joint component, the intermediate component including the bearing surface. When the modular joint prosthesis is a total knee prosthesis, the first component is the femoral component, the second component is the tibial component and the intermediate is the meniscal component.

The second joint component can define a bore, while the intermediate component can includes a pin sized to be received within the bore. The bore and pin can be configured to permit relative rotation therebetween when the pin is received within the bore to add a rotational degree of freedom between the femoral and tibial components.

In one aspect of the invention, the mating component or the intermediate component defines an elongated channel. The stabilizing post includes a base configured for sliding engagement within the channel and a spine projecting from the base through the channel and into the recess when the articular surface is in contact with the bearing surface. In certain embodiments, the channel is open at one end. In these embodiments, a locking member can be provided that is configured to close the one end with the base of the stabilizing post disposed within the channel. The locking member can be configured for a press-fit within the channel.

In some embodiments, the channel includes an enlarged groove at opposite sides of the channel. The base of the stabilizing post can then be configured for sliding engagement within the grooves, while the locking component can be configured for locking engagement within the grooves. Preferably, the channel has a length greater than the length of the base so that the base can translate within the channel.

The recess of the first joint component can define surfaces at its opposite ends. The stabilizing post preferably includes a face opposing each of the opposite end surfaces. The recess surfaces and a corresponding opposing face of the stabilizing post are configured to provide a camming movement of the stabilizing post as the recess end surface moves in contact with the opposing face. Thus, as the first joint component rolls and translates relative to the mating component, the camming movement causes the stabilizing post to slide between the ends of the channel.

In some embodiments, two faces of the stabilizing post are differently curved to provide different camming effects at opposite ends of the channel. In one feature of these embodiments, a plurality of stabilizing posts can be provided having different profiles. An appropriate stabilizing post can be selected during a total knee procedure to optimize the movement of the resulting prosthetic joint.

It is one object of the present invention to provide a prosthetic joint that permits relative rolling and translation between two bone engaging components. A further object is achieved by features of the invention that reduce the exposure of articulating surfaces and components of the prosthetic joint to soft tissue surrounding the joint.

These objects and certain benefits of the invention can be ascertained from the following written description taken together with the accompanying figures.

DESCRIPTION OF THE FIGURES

FIG. 1 is an exploded perspective view of the components of a joint prosthesis in accordance with one embodiment of the invention.

FIG. 2 is a side exploded view of the intermediate component of the joint prosthesis shown in FIG. 1.

DESCRIPTION OF THE PREFERRED EMBODIMENTS

Figure 3:
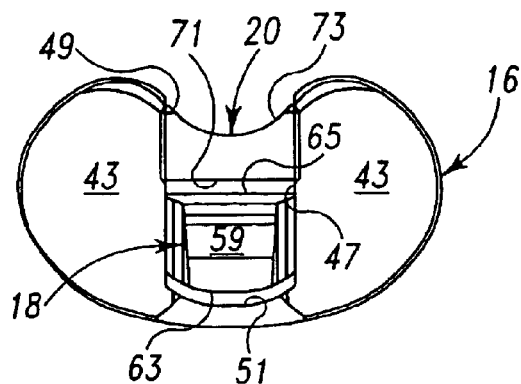
FIG. 3 is a top elevational view of the intermediate component shown in FIG. 2.
Figure 4:
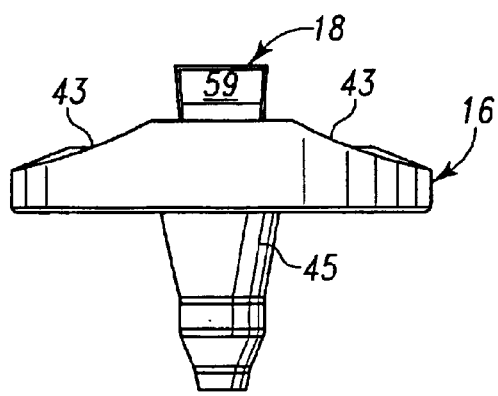
FIG. 4 is an end elevational view of the intermediate component shown in FIG. 2.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring first to FIG. 1, a modular joint prosthesis 10 is depicted that comprises a first joint component 12, a second joint component 14 and an intermediate joint component 16. From the perspective of a knee prosthesis, the first joint component 12 can be referred to as the femoral component, the second joint component 14 as the tibial component, and the intermediate joint component 16 as the meniscal component.

The femoral and tibial components can be configured according to known designs for these elements. For the purposes of the present disclosure, certain details of these components will be described. The femoral component 12 can include an articular surface, or more particularly a pair of condylar articular surfaces 25. These surfaces are smoothly curved and configured to emulate the shape of the natural femoral condyles. The component 12 also includes a bone engaging portion 27 which can include fixation posts 28. The bone engaging portion 27 can be configured in a known manner for attachment to the distal femur. The femur can be prepared in a conventional manner to accept the femoral component 12.

The femoral component 12 can further include a patellar element 30 that is integral with the articular surfaces 25. A separate patellar element can also be provided for connection to the femoral component. The component 12 also includes an intercondylar recess 32 which is preferably a box-like structure spanning the AP dimension of the component. A slot 33 can be included in the proximal face of the recess 32. In one feature of the femoral component 12 of the present embodiment, a tab 34 can be provided at the posterior end of the recess 32. The tab 34 can operate as a control for roll-back of the tibia relative to the femur as the joint is articulated.

The tibial component 14 can be in the form of a conventional tibial tray. The component includes a proximal surface 35 that parallels the tibial plateau cut into the proximal end of the tibia to receive the component. A fixation stem 37 projects downwardly from the tibial tray and is configured for solid, permanent fixation within the prepared end of the tibia. A connection bore 39 extends from the proximal surface 35 into the fixation stem 37. The bore is configured to receive a mating stem 45 of the intermediate joint component 16 in a known fashion. To approximate the shape of the prepared end of the tibia, the tibial component 14 can define a posterior recess 41.

Turning now to the intermediate component 16, details of its design can be gleaned from FIGS. 1–4. In general, the intermediate component can be configured like similar components from known modular knee prostheses. Thus, the intermediate component 16 can include opposite spaced-apart bearing surfaces 43 that are configured for articulating contact with the articular surfaces 25 of the femoral component 12. The component 16 can also include a rotation pin 45 that is rotatably mounted within the connection bore 39 of the tibial component 14. The interface between the rotation pin and the tibial component bore can be of conventional design that permits relative rotation between the intermediate component 16 and the patient's tibia. In the illustrated embodiment, the axis of rotation of the intermediate component 16 is at the center of the component and of the tibial component 14; however, other axes of rotation are contemplated as required for the particular joint anatomy and the desired movement of the joint prosthesis.

In a modification from prior intermediate components, the component 16 of the present invention includes a channel 47 defined between the spaced-apart bearing surfaces 43. In general, the position of the channel 47 corresponds to the position of the recess 32 of the femoral component 12 when the two components 12 and 16 are in articulating contact. The channel 47 can include a posterior opening 49 at the posterior side of the intermediate component 16. A stop surface 51 is provided at the closed anterior end of the channel 47. Opposite grooves 53 can be formed at the base of the channel 47 for reasons set forth below. As shown in the figures, the channel 47 extends substantially along the entire AP length of the intermediate joint component 16.

The channel 47 is configured to receive a further novel component of the prosthesis 10, namely the stabilizing post 18. The stabilizing post 18 projects upward from the intermediate component 16 to engage the intercondylar recess 32 in the femoral component 12. As best illustrated in FIGS. 1 and 2, the stabilizing post 18 includes a base 55 that is sized for sliding engagement within the grooves 53 of the channel 47. The base 55 and grooves 53 preferably form a close running fit so that the stabilizing post 18 can slide freely within the channel 47 without binding.

The stabilizing post 18 includes a spine 57 that projects from the base 55. The spine 57 is sized for sliding movement along the exposed length of the channel 47 facing the femoral component recess 32. The spine 57 has a height from the base 55 that is sufficient to span the height of the recess 32 and extend at least partially into the slot 33 when the femoral component and intermediate component are in articulating contact. The spine 57 serves to limit the AP movement of the femoral component 12. In addition, a close running fit between the spine 57 and the recess 32 helps ensure that the femoral component 12 does not rotate relative to the intermediate component 16, even when the tibial component rotates relative to the intermediate component.

As shown in FIGS. 1–3 and 5, the joint prosthesis also includes a locking member 20 that closes the posterior opening 49 of the channel 47. Thus, the locking member 20 retains the stabilizing post 18 within the channel 47. The locking member includes locking edges 69 on opposite sides of the member that are configured for locking engagement within the grooves 53 at the posterior end of the channel 47. The locking edges 69 and grooves 53 can be configured to achieve a variety of locking engagements therebetween to essentially permanently connect the two parts together and close the posterior opening of the channel. Thus, in one embodiment, the locking edges and grooves can form a press-fit engagement. In a specific embodiment, the press-fit engagement can be accomplished by complementary Morse taper angles. In another embodiment, the locking edges and grooves can be configured for a snap-fit engagement, sock as a locking tab and notch configuration. In yet another alternative, an independent fixation, such as a screw of even epoxy, can be used to lock the locking member 20 within the end of the channel.

Figure 5:
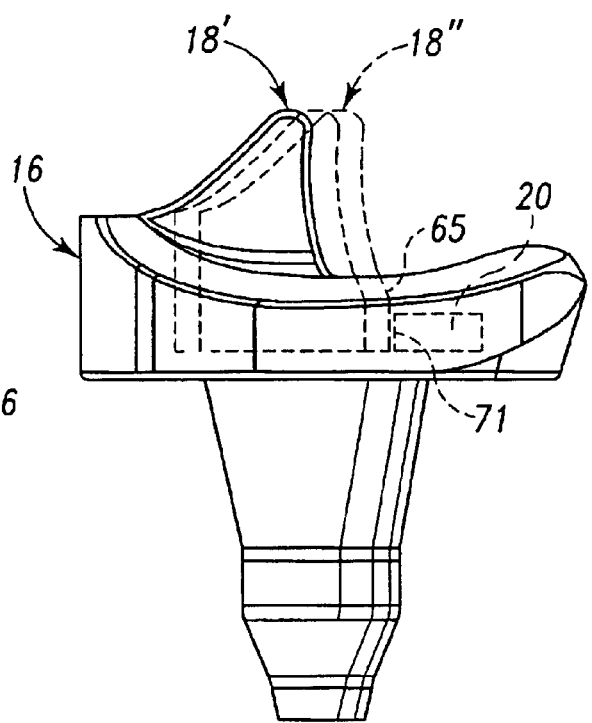
FIG. 5 is a side elevational view of the intermediate component shown in FIG. 2, with the stabilizing post shown in different positions.

The locking member 20 operates to trap the stabilizing post 18 within the channel. Thus, the member includes a stop surface 71 facing the posterior end 65 of the post 18. The stabilizing post also includes an opposite anterior end 63 that contacts the closed end 51 of the channel 47. The stabilizing post can thus move along the length of the channel from an anterior position 18' to a posterior position 18", as depicted in FIG. 5.

Figure 6:
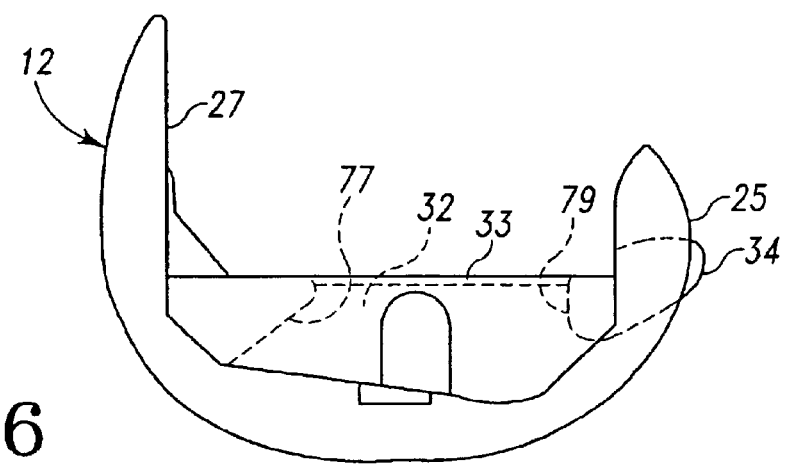
FIG. 6 is a side elevational view of the femoral component of the prosthetic joint shown in FIG. 1.

The spine 57 of the stabilizing post 18 includes an anterior face 59 and an opposite posterior face 61. Each face exhibits a pre-defined curvature for cammed movement of the stabilizing post during articulation of the femoral component 12 on the intermediate component 16. In order to achieve this cammed movement, the femoral component, and more particularly the intercondylar recess 32, defines a posterior-facing cam surface 77 at one end of the recess and an anterior-facing cam surface 79 at the opposite end of the recess, as shown best in FIG. 6. In essence, the two cam surfaces 77, 79 extend from the posterior and anterior ends of the slot 33 (FIG. 1). These cam surfaces bear against a corresponding face 59, 61 of the spine 57 to urge the stabilizing post 18 along the channel in the AP direction. This feature allows the femoral component 12 to both roll and slide relative to the tibial component without exposing the articulating components and surfaces to the soft tissue surrounding the joint.

Figure 8:
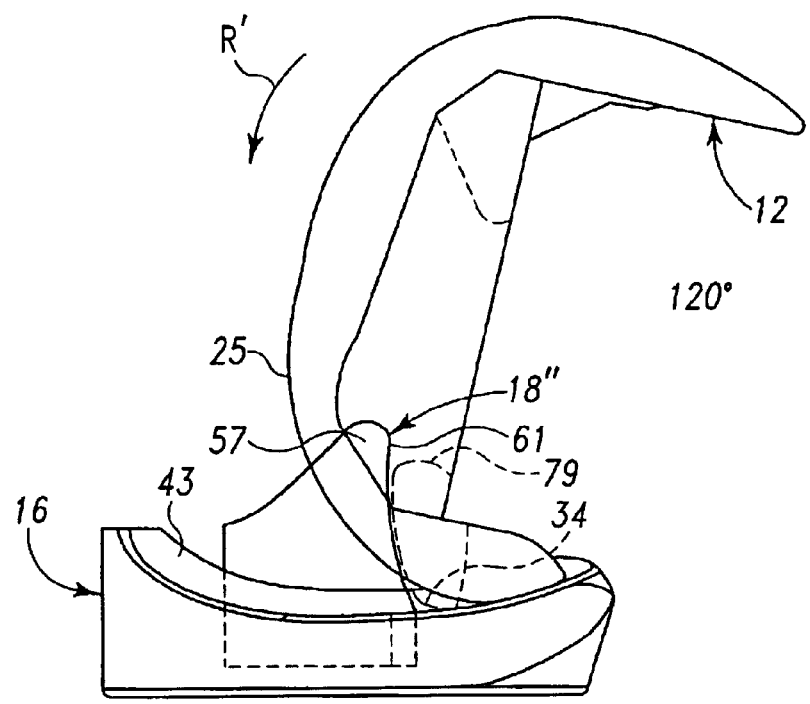
FIG. 8 is a side elevational view showing another position of the femoral component relative to the intermediate component of the prosthetic joint shown in FIG. 1.
Figure 7:
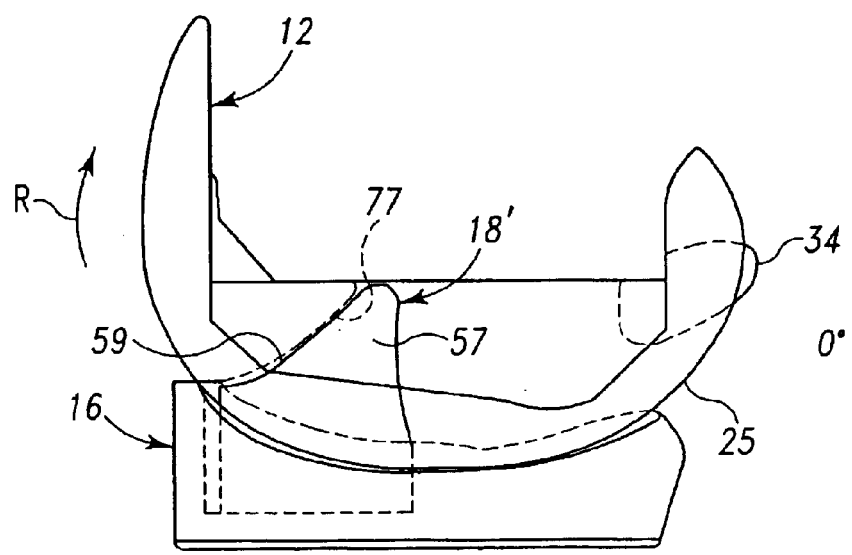
FIG. 7 is a side elevational view showing one position of the femoral component relative to the intermediate component of the prosthetic joint shown in FIG. 1.

This rolling and sliding movement can be appreciated from a comparison of FIGS. 7 and 8. In FIG. 7, the stabilizing post 18 is in its anterior position 18' and the femur and femoral component 12 is essential at its zero degree angle relative to the tibia and tibial component 14. The posterior-facing cam surface 77 bears against the anterior face 59 of the spine 57. As the femoral component 12 begins to roll in the direction of the arrow R (FIG. 7), the cam surface 77 bears against the anterior face 59 of the spine 57 to push the stabilizing post 18 posteriorly. Eventually, the post is pushed to its posterior position 18", as shown in FIG. 8. The slope and curvature of the anterior face 59 dictates the degree and speed of travel of the post along the channel 47.

Once the stabilizing post is in its posterior position 18", the camming surface 77 no longer contacts the spine 57 as the femoral component continues to roll and translation anteriorly relative to the tibial component. Eventually, the femoral component is in the relative position shown in FIG. 8 in which the femur is at an angle of about 120° relative to the tibia. The tab 34 engages the posterior indentation 73 in the locking member 20 to prevent further relative rolling and translation (in conjunction with tension in the collateral ligaments). In this position, the anterior-facing cam surface 79 contacts the posterior face 61 of the spine 57.

As the femoral component undergoes relative rolling in the opposite direction, as designated by the arrow R' in FIG. 8, the cam surface 79 bears against the posterior face 61 to push the spine 57 anteriorly along the channel. When the cam surface 79 breaks contact with the spine, the stabilizing post is in its relative anterior position 18' (FIG. 7). The spine thus prevents further anterior relative translation of the femoral component 12. Again, it can be seen that none of the articulating surfaces or components impinge or are exposed to the surround soft tissue, even where the femoral component moves between the extreme relative positions shown in FIGS. 7 and 8.

The sliding stabilizing post 18 of the present invention provides a significant advantage during the total knee replacement procedure. In specifically, the specific post can be selected during the procedure and tested to verify optimum knee movement for the particular patient. In other words, while the post 18 shown in the present figures exhibits a certain configuration, an array of posts can be available, all with different profiles. For instance, the posts can be configured to permit greater or lesser movement within the channel 47. In addition, one or both of the faces 59, 61 can be modified to achieve a specific camming action when contacted by the femoral component cam surfaces 77, 79.

Thus, in accordance with one feature of the present invention, the femoral and tibial components 12, 14 can be prepared bone surfaces. The intermediate or meniscal component 16 can be mounted to the tibial component 14 with the knee in flexion. A pre-selected stabilizing post 18 can be slid into the channel 47 and a temporary locking member can close the post within the channel. The knee can then be moved with the prosthesis in situ through certain degrees of motion to determine whether the selected post is optimum for the particular patient's anatomy. If not, the post can be removed and replaced with a different post having a different profile. Once an optimum stabilizing post has been found, the locking member 20 can be connected to the intermediate component 16 to lock the finally selected post 18 within the channel 47.

The same process can be followed with respect to the locking member 20. Locking members having different lengths along the channel can be provided to allow more or less sliding movement of the stabilizing post 18 within the channel 47. In some cases, a locking member can be selected that does not permit any sliding of the post 18.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, the intermediate component 16 may be made integral with the tibial component 14. In this case, the rotational degree of freedom would be eliminated.

In addition, the engagement of the stabilizing post 18 to the channel 47 can be modified so that the both ends of the channel are closed. For example, the channel can be provided with an enlarged top opening and the base 55 of the post 18 can be configured to fit through the enlarged opening and then pivot to engage the grooves 53 at the base of the channel. Engagement of the spine 57 within the intercondylar recess 32 will prevent pivoting of the post once it is disposed within the channel.

In the illustrated embodiment, the channel 47 is described as including one closed end 51 and an opposite open end 49. Alternatively, both ends of the channel can be open with a corresponding locking member, such as the locking member 20, closing each end to trap the stabilizing post 18 within the channel. The two locking members can be selected intra-operatively to optimize and orient the translation of the stabilizing post within the channel.

What is claimed is:

1. A joint prosthesis, comprising:
   a femoral component having first condylar articular surface, a second condylar articular surface, and an intercondylar recess interposed therebetween;
   a tibial component having a bone engaging portion and defining a connection bore;
   a meniscal component having a stem positioned within said connection bore of said tibial component so as to rotatably mount said meniscal component to said tibial component, and further having a first bearing surface and a second bearing surface spaced apart from each other so as to define a channel; and
   a stabilizing post slidably mounted within said channel of said meniscal component, said post projecting into said intercondylar recess when said first condylar articular surface and said second condylar articular surface are respectively positioned in contact with said first bearing surface and said second bearing surface,
   wherein no relative movement occurs between said stem and said first bearing surface and said second bearing surface during sliding of said stabilizing post within said channel of said meniscal component.

2. The joint prosthesis of claim 1, wherein said channel includes an open end, and further comprising:
   a locking member configured to be mounted in said open end of said channel.

3. The joint prosthesis of claim 2, wherein said locking member provides a stop surface at said open end of said channel when said locking member is mounted in said open end of said channel.

4. The joint prosthesis of claim 2, wherein said locking member is configured to be press-fit within said channel.

5. The joint prosthesis of claim 1, wherein:
   said channel defines a pair of grooves, each being located at a lateral side of said channel, and
   said stabilizing post includes a base configured for sliding engagement within said pair of grooves.

6. The joint prosthesis of claim 5, wherein said base has a first length and said channel has a second length greater than said first length.

7. The joint prosthesis of claim 5, further comprising a locking component configured for locking engagement within said pair of grooves.

8. The joint prosthesis of claim 1, further comprising a plurality of locking components each configured for locking engagement within said pair of grooves, wherein each of said plurality of locking members possesses a different length.

9. The joint prosthesis of claim 1, further comprising a number of alternate stabilizing posts each configured to mount within said channel of said meniscal component, wherein each of said number of alternate stabilizing posts possesses a profile that is different from others of said number of alternate stabilizing posts.

10. The joint prosthesis of claim 1, wherein:
    said intercondylar recess includes surfaces at its opposite ends;
    said stabilizing post includes a face opposing one of said opposite end surfaces; and
    said face and said one of said opposite end surfaces are configured to provide a camming movement of said stabilizing post as said one of said opposite end surfaces moves in contact with said face.

11. The joint prosthesis of claim 10, wherein:
    said stabilizing post includes an opposite face opposing the other of said opposite end surfaces; and
    said opposite face and the other of said opposite end surfaces are configured to provide a camming movement of said stabilizing post as said other of said opposite end surfaces moves in contact with said opposite face.

12. The joint prosthesis of claim 11, wherein said face and said opposite face are differently curved.

13. A joint prosthesis, comprising:
    a femoral component having a first bone engaging portion, an articular surface, and a recess formed in said articular surface;
    a tibial component having a second bone engaging portion and defining a bore;
    a meniscal component having (i) a stem positioned within said bore of said tibial component, and (ii) a bearing surface configured to contact said articular surface, said meniscal component defining a channel; and
    a stabilizing post slidably mounted within said channel, said post projecting into said recess when said articular surface is positioned in contact with said bearing surface,
    wherein no relative movement occurs between said stem and said bearing surface during sliding of said stabilizing post within said channel.

14. The joint prosthesis of claim 13, wherein said meniscal component is configured to rotate in relation to said tibial component.

15. The joint prosthesis of claim 13, wherein said meniscal component includes a first bearing surface and a second bearing surface spaced apart from each other so as to define said channel.

16. A joint prosthesis comprising:
    a first joint component having a bone engaging portion, an articular surface, and a recess defined within said articular surface;
    a mating component having a bone engaging portion and defining a bearing surface for sliding contact with said articular surface of said first joint component; and
    a stabilizing post slidably mounted to said mating component amid said bearing surface, said post projecting from said mating component and into said recess when said articular surface is in contact with said bearing surface, wherein said mating component includes (i) a second joint component including the bone engaging portion; and (ii) an intermediate component connected to said second joint component, said intermediate component including said bearing surface, wherein said second joint component defines a bore; and wherein said intermediate component includes a pin sized to be received within said bore, and wherein no relative movement occurs between said pin and said bearing surface during sliding of said stabilizing post relative to said intermediate component of said mating component.

17. The joint prosthesis of claim 16, wherein said bore and said pin are configured to permit relative rotation therebetween when said pin is received within said bore.

18. The joint prosthesis of claim 16, wherein:

said mating component defines an elongated channel; and said stabilizing post includes a base configured for sliding engagement within said channel and a spine projecting from said base through said channel and into said recess when said articular surface is in contact with said bearing surface.

19. The joint prosthesis of claim 18, wherein:

said channel is open at one end; and said mating component includes a locking member configured to close said one end with said base of said stabilizing post disposed within said channel.

20. The joint prosthesis of claim 19, wherein said locking member is configured for a press-fit within said channel.

21. The joint prosthesis of claim 19, wherein:

said channel includes an enlarged groove at opposite sides of said channel;

said base is configured for sliding engagement within said grooves; and said locking component is configured for locking engagement within said grooves.

22. The joint prosthesis of claim 19, wherein said locking member is selectable from a plurality of locking members having different lengths when disposed within said channel.

23. The joint prosthesis of claim 18, wherein:

said channel includes an enlarged groove at opposite sides of said channel; and said base is configured for sliding engagement within said grooves with said spine projecting through said channel.

24. The joint prosthesis of claim 23, wherein said base has a length and said channel has a length greater than the length of said base.

25. The joint prosthesis of claim 16, wherein said stabilizing post is selectable from a plurality of stabilizing posts having different profiles.

26. The joint prosthesis of claim 16, wherein:

said recess includes surfaces at its opposite ends;

said stabilizing post includes a face opposing one of said opposite end surfaces; and said face and said one of said opposite end surfaces are configured to provide a camming movement of said stabilizing post as said one of said opposite end surfaces moves in contact with said face.

27. The joint prosthesis of claim 26, wherein:

said stabilizing post includes an opposite face opposing the other of said opposite end surfaces; and said opposite face and the other of said opposite end surfaces are configured to provide a camming movement of said stabilizing post as said other of said opposite end surfaces moves in contact with said opposite face.

28. The joint prosthesis of claim 27, wherein said face and said opposite face are differently curved.

* * * * *